US00PP30994P3

(12) United States Plant Patent
van Langen

(10) Patent No.: US PP30,994 P3
(45) Date of Patent: Oct. 29, 2019

(54) ***PACHYVERIA* PLANT NAMED 'TSAECH1705'**

(50) Latin Name: **x *Pachyveria* spp.**
Varietal Denomination: TSAECH1705

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 15/932,698

(22) Filed: Apr. 10, 2018

(65) Prior Publication Data

US 2018/0310455 P1 Oct. 25, 2018

(30) Foreign Application Priority Data

Apr. 19, 2017 (QZ) ..... PBR 2017/1056

(51) Int. Cl.
*A01H 5/12* (2018.01)
*A01H 6/32* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ... A01H 5/12; A01H 5/00; A01H 5/02; A01H 6/32
See application file for complete search history.

(56) References Cited

PUBLICATIONS

Community Plant Variety Office application No. 2017/1056 for x *Pachyveria* 'TSAECH1705' filed on Apr. 19, 2017, 17 pp. (Year: 2017).*

* cited by examiner

*Primary Examiner* — June Hwu
(74) *Attorney, Agent, or Firm* — Samuel R. McCoy, Jr.

(57) ABSTRACT

A new and distinct *Pachyveria* plant named 'TSAECH1705' which is characterized by an abundance of succulent foliage arranged in large basal rosette, foliage at the center of the rosette with an attitude that varies from upright to somewhat relaxed in response to changing weather, foliage which is generally grey in color and moderately suffused with pink, as well as the stability of these characteristics from generation to generation.

4 Drawing Sheets

Latin name of the genus and species: The Latin name of the genus and species of the novel variety disclosed herein is x *Pachyveria* spp.

Variety denomination: The inventive variety of *Pachyveria* hybrid disclosed herein has been given the variety denomination 'TSAECH1705'.

CROSS REFERENCE TO RELATED APPLICATIONS

This application claims priority to the Community Plant Variety Rights application number 2017/1056, filed Apr. 19, 2017, which is herein incorporated by reference.

BACKGROUND OF THE INVENTION

Parentage: 'TSAECH1705' is an intergeneric hybrid seedling selection resulting from the controlled pollination of an unnamed *Pachyphytum glutinicaule* x *Pachyphytum oviferum* hybrid plant (not patented), the seed parent, with *Echeveria pulidonis* x *Echeveria* hybrid 'Perle von Nurnberg' (not patented), the pollen parent. The crossing was made by the inventor in the summer of 2013 at a commercial greenhouse in Heerhugowaard, the Netherlands. In the summer of 2014, one seedling was observed which exhibited unique growth and foliage characteristics. The seedling was isolated for further evaluation in order to confirm the distinctness and stability of the characteristics first observed. Upon confirmation of distinctness and stability, 'TSAECH1705' was selected for commercialization in the autumn of 2014.

Asexual Reproduction: Asexual reproduction of the new cultivar 'TSAECH1705', by way of rooting leaf cuttings, was first initiated in the spring of 2015 at the inventor's commercial greenhouse in Heerhugowaard, the Netherlands. Through five subsequent generations, the unique features of this cultivar have proven to be stable and true to type.

SUMMARY OF THE INVENTION

The cultivar 'TSAECH1705' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1705'. These characteristics in combination distinguish 'TSAECH1705' as a new and distinct *Pachyveria* cultivar:

1. 'TSAECH1705' exhibits an abundance of succulent foliage arranged in large basal rosette; and
2. 'TSAECH1705' exhibits broad spatulate to obovate foliage which is moderately concave and moderately curved upwards; and 3. 'TSAECH1705' exhibits foliage at the center of the rosette with an attitude that varies from upright to somewhat relaxed in response to changing weather; and
4. 'TSAECH1705' exhibits foliage which is generally grey in color and moderately suffused with pink.

BOTANICAL DESCRIPTION OF THE PLANT

Figure 1:
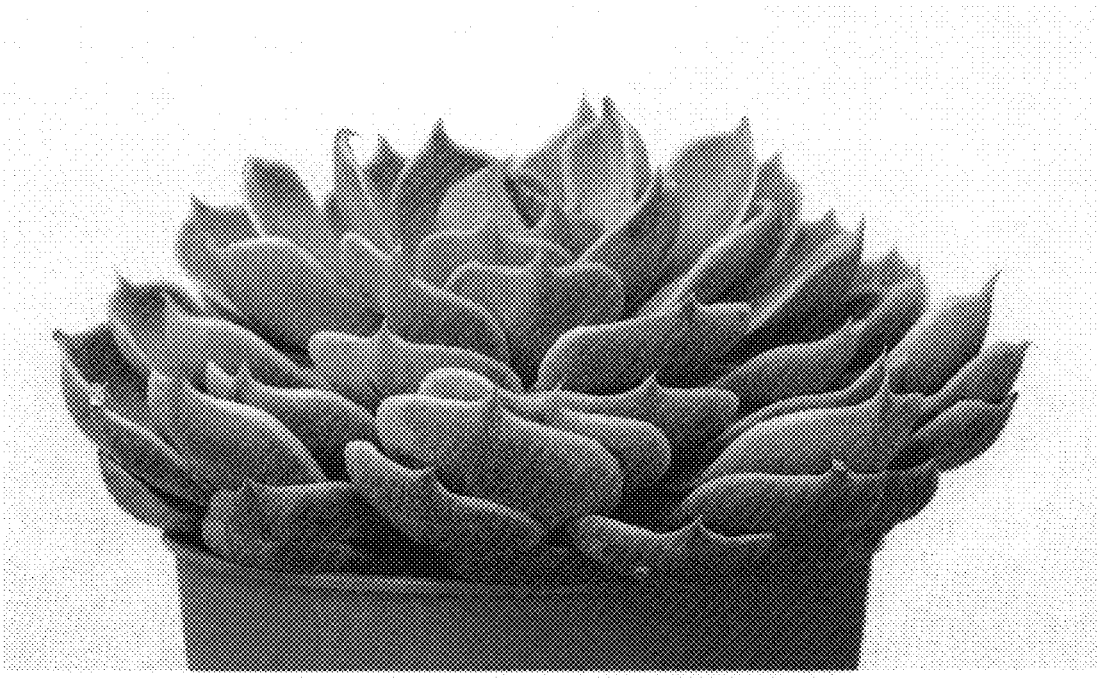
FIG. 1 illustrates, as nearly true as it is reasonably possible to make the same in color photographs of this type, an exemplary plant of 'TSAECH1705' grown in a commercial greenhouse in Heerhugowaard, the Netherlands. This plant is approximately 12 months old, shown planted in a 12 cm container.
Figure 2:
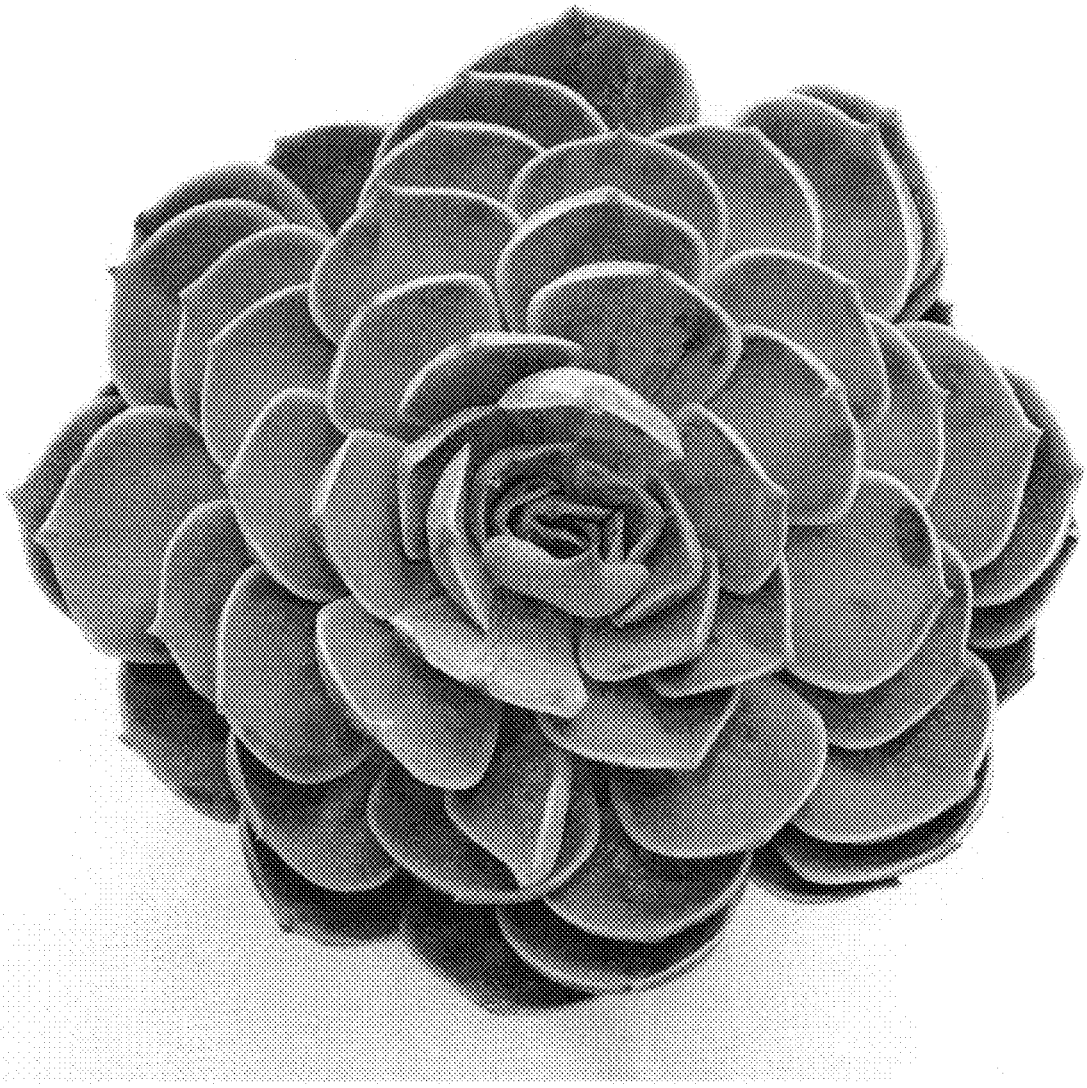
FIG. 2 illustrates, as nearly true as it is reasonably possible to make the same in color photographs of this type, the typical foliage arrangement of 'TSAECH1705.
Figure 3:
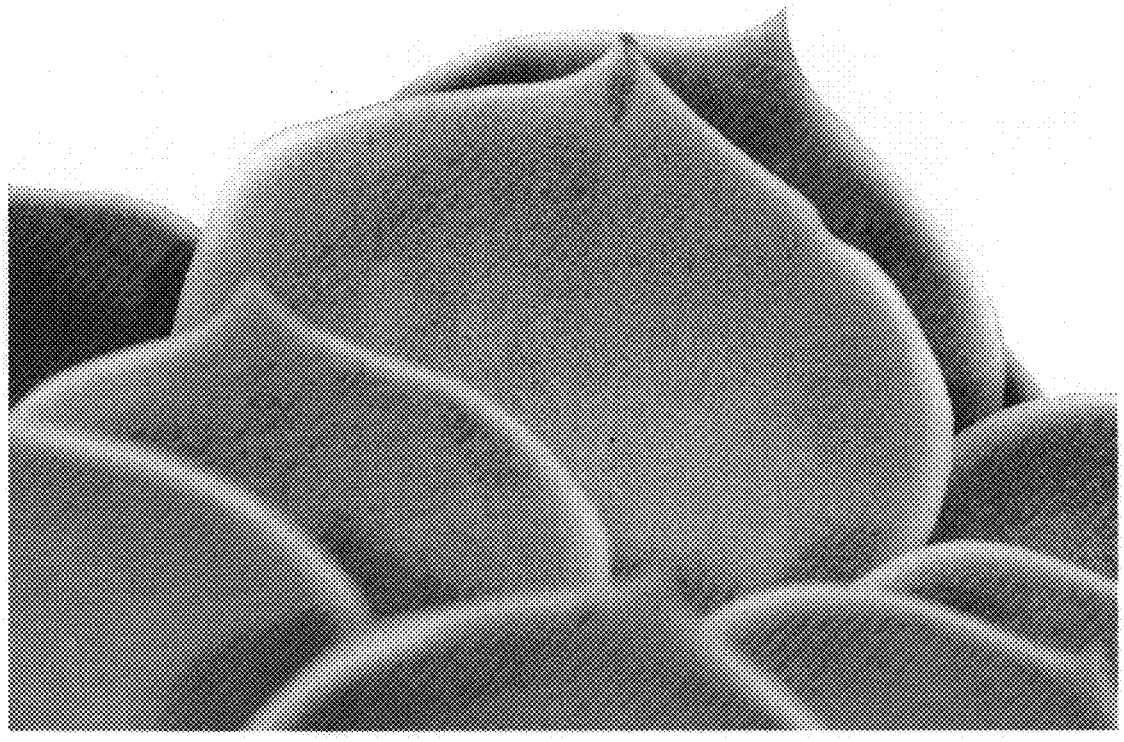
FIG. 3 illustrates, as nearly true as it is reasonably possible to make the same in color photographs of this type, the adaxial surface of the mature foliage of 'TSAECH1705'.
Figure 4:
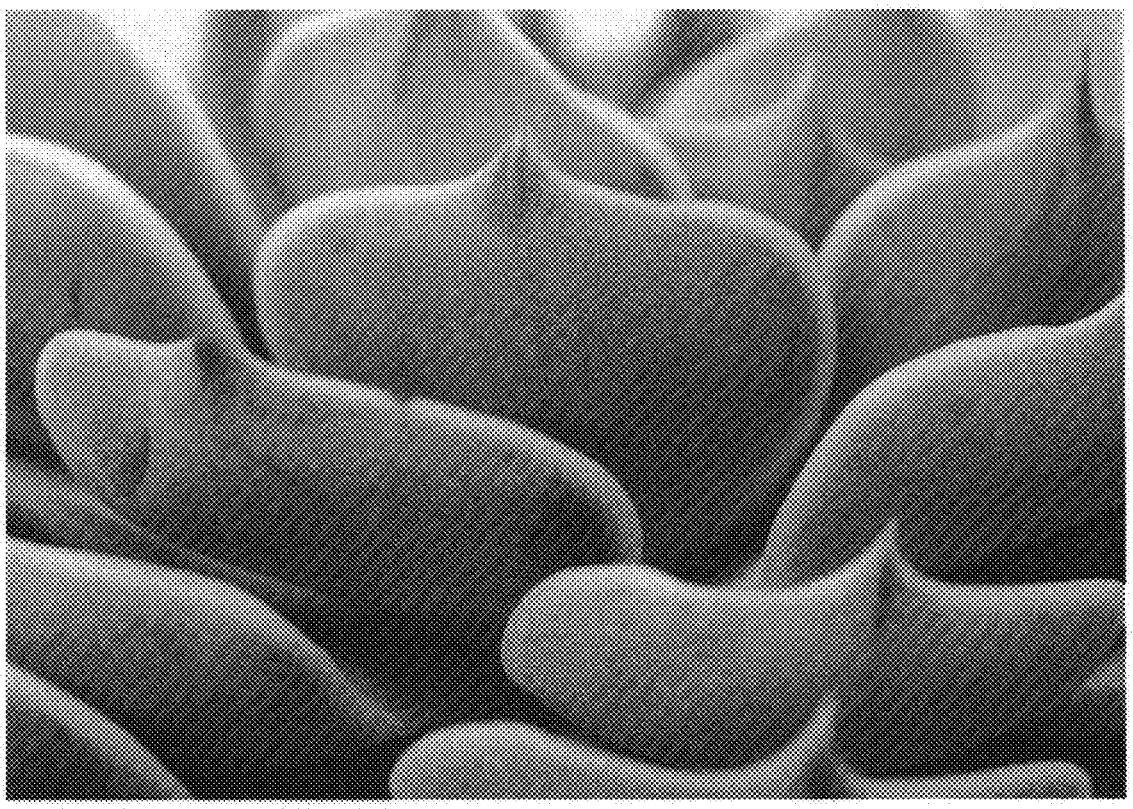
FIG. 4 illustrates, as nearly true as it is reasonably possible to make the same in color photographs of this type, the abaxial surface of the mature foliage 'TSAECH1705'.

The following observations and measurements made in March of 2018 describe averages from a sample set of six specimens of 12 months old 'TSAECH1705' plants grown in 12 cm nursery containers at commercial greenhouse in Heerhugowaard, the Netherlands. Plants were produced using conventional greenhouse production protocols for *Echeveria* and *Pachyphytum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1705' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1705' and comparisons with the parent plants and closest known comparator are provided below.

Plant description:

*Growth habit.*—Succulent perennial with foliage growing in a non-branched basal rosette.

*Plant shape.*—Flattened globular.

*Height from soil level to top of foliar plane.*—8.4 cm.

*Plant spread.*—Average of 16.8 cm.

*Growth rate.*—Moderate.

*Plant vigor.*—Moderate.

*Propagation.*—Type — Leaf cuttings. Time to initiate rooting — Approximately 21 days at 18 degrees Celsius. Crop time — Approximately 35 weeks to produce a marketable plant in an 11 cm container.

*Disease and pest resistance or susceptibility.*—Neither resistance nor susceptibility to typical *Echeveria* and *Pachyphytum* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 68 leaves per rosette.

*Shape.*—Thick, succulent leaves which are broad spatulate to obovate.

*Dimensions.*—7.4 cm long, 3.9 cm wide, and 0.6 cm thick, on average.

*Aspect.*—Moderately concave and moderately curved upward.

*Attitude.*—Younger foliage near the center of the rosette is very upright; foliage becoming progressively more relaxed towards the outer whorl of the rosette.

*Apex.*—Broad acute to apiculate with the tip curled upward.

*Base.*—Cuneate.

*Margin.*—Entire; not undulated or lobed.

*Pubescence, texture and luster of the adaxial surface.*—Glabrous, smooth, and matte; moderately glaucous.

*Pubescence, texture and luster of the abaxial surface.*—Glabrous, smooth, and matte; moderately glaucous.

*Color.*—Juvenile foliage, adaxial surface — Yellow-green, nearest to a mixture of RHS 147B and 148B; distal half and apex are narrowly margined greyed-red, nearest to RHS 181D, and the proximal half is narrowly margined white, nearest to RHS 155C; the epicuticular glaucous wax covering the leaf surface is greyed-green, nearest to in between RHS 188A and 198B. Juvenile foliage, abaxial surface — Yellow-green, nearest to RHS N148C, and suffused with greyed-red towards the apex, nearest to a mixture of RHS 182C and 182D; distal half and apex are narrowly margined greyed-red, nearest to RHS 182C, and the proximal half is narrowly margined white, nearest to RHS 155A; the epicuticular glaucous wax covering the leaf surface is greyed-purple, nearest to a mixture of RHS N187C and N187D. Mature foliage, adaxial surface — In between yellow-green and greyed-green, nearest to RHS 148A and 197A, and fading to greyed-green towards the base, nearest to RHS 195B; tipped and narrowly margined white, nearest to RHS 155A; the epicuticular glaucous wax covering the leaf surface is greyed-green, nearest to in between RHS 188A and 198B. Mature foliage, abaxial surface — Yellow-green, nearest to RHS 148A, and moderately suffused with greyed-red, nearest to a mixture of RHS 182B and 182C; tipped and narrowly margined green-white, nearest to a mixture of RHS 156C and 156D; the epicuticular glaucous wax covering the leaf surface is greyed-purple, nearest to a mixture of RHS N187C and N187D.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1705' differ from the seed parent, an unnamed *Pachyphytum glutinicaule* x *Pachyphytum oviferum* hybrid plant (not patented), in the following characteristics described in Table 1 below.

TABLE 1

| Characteristic | 'TSAECH1705' | Unnamed *Pachyphytum* hybrid seed parent. |
|---|---|---|
| Leaf thickness. | Thinner than the seed parent. | Thicker than 'TSAECH1705'. |
| Lear cross-section. | Flattened. | Rounded. |
| Leaf apex. | Broad acute to apiculate. | Obtuse. |

Plants of the new cultivar 'TSAECH1705' differ from the pollen parent, *Echeveria* hybrid 'Perle von Nurnberg' (not patented), in the following characteristics described in Table 2 below.

TABLE 2

| Characteristic | 'TSAECH1705' | 'Perle von Nurnberg' |
|---|---|---|
| General coloration of the foliage. | Greyed-green and moderately suffused pink. | Greyed-green and heavily suffused pink. |
| Leaf thickness. | Thicker than 'Perle von Nurnberg'. | Thinner than 'TSAECH1705'. |

TABLE 2-continued

| Characteristic | 'TSAECH1705' | 'Perle von Nurnberg' |
|---|---|---|
| Leaf attitude in the central whorls of the rosette. | Opens and close. | Unchanging. |

COMPARISONS WITH THE CLOSEST KNOWN COMPARATOR

Plants of the new cultivar 'TSAECH1705' differ from the closest known commercial comparator, the common form of the species *Echeveria lilacina* (not patented), in the following characteristics described in Table 3 below.

TABLE 3

| Characteristic | 'TSAECH1705' | *Echeveria lilacina* |
|---|---|---|
| Growth rate. | Faster than *Echeveria lilacina*. | Slower than 'TSAECH1705'. |
| Plant size. | Larger than *Echeveria lilacina*. | Smaller than 'TSAECH1705'. |
| General coloration of the foliage. | Greyed-green and moderately suffused pink. | Very light grey, almost white, with lilac hues. |
| Leaf attitude in the central whorls of the rosette. | Opens and closes. | Unchanging |

That which is claimed is:

1. A new and distinct variety of *Pachyveria* hybrid plant named 'TSAECH1705', substantially as described and illustrated herein.

* * * * *